United States Patent [19]

Sicheneder et al.

[11] Patent Number: 5,286,870

[45] Date of Patent: Feb. 15, 1994

[54] PROCESS FOR THE PRODUCTION OF BIS-BENZTHIAZOLYL ALKYL SULFENIMIDES

[75] Inventors: Adolf Sicheneder, Dormagen; Harro Schlesmann, Odenthal, both of Fed. Rep. of Germany

[73] Assignee: Bayer AG, Leverkusen, Fed. Rep. of Germany

[21] Appl. No.: 931,205

[22] Filed: Aug. 17, 1992

[30] Foreign Application Priority Data

Aug. 29, 1991 [DE] Fed. Rep. of Germany ........ 4128682

[51] Int. Cl.$^5$ ............................................ C07D 417/12
[52] U.S. Cl. .................................................... 548/157
[58] Field of Search ......................................... 548/157

[56] References Cited

U.S. PATENT DOCUMENTS 2,860,142  11/1958  Conly ................................... 548/157
2,873,277   2/1959  Sundholm ............................ 548/157
3,737,431   6/1973  Campbell et al. ................... 548/167
4,182,873   1/1980  Janin ................................... 544/133
4,461,897   6/1984  Cobb et al. ......................... 548/167

FOREIGN PATENT DOCUMENTS 1181659  6/1959  France .
0813968  5/1959  United Kingdom .
1407649  9/1975  United Kingdom .

Primary Examiner—Joseph Paul Brust
Assistant Examiner—MarySusan H. Gabilan
Attorney, Agent, or Firm—Connolly and Hutz

[57] ABSTRACT

Bis-benzthiazolyl alkyl sulfenimides are produced by a process in which alkyl amines are reacted with optionally substituted 2-mercaptobenzthiazoles in the presence of oxygen or oxygen-containing gases and copper and/or copper compounds and in the presence of inert organic solvents.

15 Claims, No Drawings

PROCESS FOR THE PRODUCTION OF BIS-BENZTHIAZOLYL ALKYL SULFENIMIDES

This invention relates to a process for the production of bis-benzthiazolyl alkyl sulfenimides from optionally substituted 2-mercaptobenzthiazoles and alkyl amines by catalyzed oxidation with oxygen. The bis-benzthiazolyl alkyl sulfenimides obtained may be used as vulcanization accelerators.

Bis-benzthiazolyl alkyl sulfenimides are known and may be obtained by reaction of 2-benzthiazolyl alkyl sulfenamides with acids or acid derivatives, such as acid anhydrides and acid chlorides. Thus, GB 1,288,701 and U.S. Pat. No. 2,860,142, for example, describe the use of carboxylic anhydrides in the production of bis-benzthiazolyl alkyl sulfenimides. According to Ignatov et al. [Zh. Obshch. Khim. 47(5), 1096], bis-benzthiazolyl alkyl sulfenimides can also be obtained by reaction of the sulfenamides with carboxylic acid chlorides. The disadvantage of the processes mentioned above is that equivalent quantities of carboxylic acid amides are formed. The carboxylic acid amides formed have to be removed from the reaction mixture so that the processes mentioned are far from economical.

In addition, bis-benzthiazolyl alkyl sulfenimides can be obtained by reaction of 2-benzthiazolyl sulfenyl chloride with alkyl amines (U.S. Pat. No. 2,873,277) or 2-benzthiazolyl alkyl sulfenamides (N. K. Sundholm, Ind. Eng. Chem. 52, 239, 1960). The disadvantage of this process lies in the poor accessibility of the sulfene chlorides to be used which are obtained in moderate yields by reaction of corresponding benzthiazolyl disulfides with chlorine.

It has now been found that bis-benzthiazolyl alkyl sulfenimides can be obtained by a process which is characterized in that alkyl amines are reacted with optionally substituted 2-mercaptobenzthiazoles in the presence of oxygen or oxygen-containing gases and copper and/or copper compounds and in the presence of organic inert solvents.

Starting out from mercaptobenzthiazole and/or the corresponding derivatives of mercaptobenzthiazole, the desired compounds are obtained in accordance with the following reaction scheme:

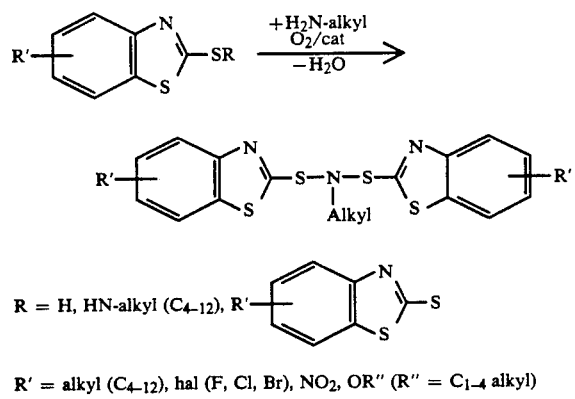

R = H, HN-alkyl (C4-12), R' = alkyl (C4-12), hal (F, Cl, Br), NO2, OR" (R" = C1-4 alkyl)

Aprotic organic solvents may be used as the inert organic solvents in the process according to the invention. For example, aliphatic and aromatic hydrocarbons, such as hexane, cyclohexane, benzene, toluene, and/or aliphatic ethers, such as ethyl, methyl tert. butyl ether, and/or aliphatic nitriles, such as acetonitrile, and/or formamides, such as dimethyl formamide, may be used in the process according to the invention. In addition, aliphatic amines with no proton at the $\alpha$-carbon atom may be used as solvents in the process according to the invention. It has proved to be of particular advantage to use tert. butyl amine or derivatives thereof as the solvent.

The solvents may be used individually or in admixture with one another.

The process according to the invention is carried out in the presence of oxygen or oxygen-containing gases, such as air, under a pressure of from about 2 to 100 bar and preferably 5 to 30 bar and at a temperature in the range from about 10° to 100° C. and preferably in the range from 40° to 70° C.

Suitable alkyl amines, with which the mercaptobenzthiazoles are reacted, are any aliphatic amines which, as mentioned above, do not bear a proton at the $\alpha$-carbon atom. Examples of such aliphatic amines are, for example, tert. butyl amine or derivatives thereof, such as 2-benzthiazolyl tert. butyl sulfenamide, and tert. amyl amine and derivatives thereof. Other aliphatic amines which do not bear a proton at the $\alpha$-carbon atom are known to the expert and may also be used. In addition to 2-mercaptobenzthiazole, the benzthiazolyl disulfides and/or 2-benzthiazolyl alkyl sulfenamides may be used.

As can be seen from the formula scheme, the mercaptobenzthiazoles and also the benzthiazolyl disulfides and the 2-benzthiazolyl alkyl sulfenamides may be substituted at the benzene ring by alkyl radicals, halogen atoms, nitro groups and alkoxy groups.

The process according to the invention is carried out in the presence of copper and/or copper compounds.

Suitable copper compounds are any inorganic, organic, simple or complex copper salts, such as the sulfates, acetates or acetyl acetonates. Copper(I) benzthiazolyl-2-mercaptide is particularly preferred.

The copper catalysts may be used in quantities of from about 0.001 to 1% by weight and preferably in quantities of 0.01 to 1% by weight, based on the mercaptobenzthiazoles used.

The quantity in which the organic inert solvents are used is between about 40 and 90% by weight and preferably from 60 to 80% by weight, based on the total weight of the reaction solution.

The process according to the invention may be carried out both continuously and also discontinuously in any suitable reactors. The optimum reaction conditions may readily be determined by preliminary tests.

EXAMPLES

Example 1

50 Parts by weight dibenzthiazyl disulfide, 71.6 parts by weight benzthiazolyl tert. butyl sulfenamide, 0.7 part by weight copper(I) benzthiazolyl-2-mercaptide and 310 parts by weight tert. butyl amine were introduced into a steel autoclave. The resulting suspension was heated to 60° C. and placed under an oxygen pressure of 11 bar. The consumption of oxygen began immediately. When the pressure had fallen to 10 bar, more oxygen was introduced so that the pressure remained in the range of 10 to 11 bar. After about 2 hours, no further significant consumption of oxygen was recorded and the test was terminated.

400 Parts by weight water were added to the reaction mixture and the amine was distilled off. The reaction mixture was then mildly acidified with 20% sulfuric acid (pH 3–4). The product was then filtered off, the filter cake was washed until neutral and the product was dried in a drying cabinet.

Yield: 87 parts by weight (72%)
Melting point: 143° C.
Purity: 99%

Example 2

100 Parts by weight 2-mercaptobenzthiazole, 0.5 part by weight copper(I) benzthiazolyl-2-mercaptide and 300 parts by weight tert. butyl amine were introduced into a steel autoclave. The resulting suspension was heated to 60° C. and placed under an oxygen pressure of 11 bar. At first, the oxygen was only slowly absorbed. After about 2 hours, the consumption of oxygen accelerated until, finally (after about 4.5 hours), no further consumption of oxygen was recorded.

The product was filtered off and dried. The dried crude product was continuously extracted with methyl tert. butyl ether in a Soxhlet extractor. After about 5 hours, the resulting suspension was filtered, the filter cake was washed with a little ether and dried.

Yield: 79 parts by weight (65%)
Content: 99%

We claim:

1. A process for the production of bis-benzthiazolyl alkyl sulfenimides, wherein alkyl amines are reacted with optionally substituted 2-mercaptobenzthiazoles in the presence of oxygen or oxygen-containing gases and a copper compound consisting essentially of copper(I)-benzthiazolyl-2-mercaptide, said process comprising:

forming a reaction mixture consisting of said alkyl amines, said optionally substituted 2-mercaptobenzthiazoles, said copper compound and at least one inert organic solvent; and contacting said reaction mixture with oxygen or oxygen-containing gases to form said bis-benzthiazolyl alkyl sulfenimides.

2. A process as claimed in claim 1, wherein the reaction is carried out at temperatures of from about 10° to 100° C. and under pressures of from about 2 to 100 bar.

3. A process as claimed in claim 1, wherein the reaction is carried out in the presence of from about 0.001 to 1% by weight of said copper compound, based on the quantity of mercaptobenzthiazole used.

4. A process as claimed in claim 1, wherein aliphatic amines with no proton at the α-carbon are used as the alkyl amines.

5. A process as claimed in claim 1, wherein the alkyl amines are used as the solvent.

6. A process as claimed in claim 1, wherein the at least one inert organic solvent consists of tert. butyl amine or derivatives thereof.

7. A process as claimed in claim 1, wherein the reaction is carried out at temperatures of from about 40° to 70° C.

8. A process as claimed in claim 1, wherein the reaction is carried out at pressures of from about 5 to 30 bar.

9. A process as claimed in claim 1, wherein the alkyl amines comprise at least one substance selected from the group consisting of tert. butyl amine, derivatives of tert. butyl amine, tert. amyl amine and derivatives of tert. amyl amine.

10. A process as claimed in clam 1, wherein the alkyl amines comprise benzthiazyl tert. butyl sulfenamide.

11. A process for the production of bis-benzthiazolyl alkyl sulfenimides wherein alkyl amines are reacted with at least one of benzthiazolyl disulfides, 2-benzthiazolyl alkyl sulfenamides and 2-mercaptobenzthiazoles in the presence of oxygen or oxygen-containing gases and a copper compound consisting essentially of copper(I)benzthiazolyl-2-mercaptide, said process comprising:

forming a reaction mixture consisting of said alkyl amines, said at least one of benzthiazolyl disulfides, 2-benzthiazolyl alkyl sulfenamides and 2-mercaptobenzthiazoles, said copper compound and at least one inert organic solvent; and contacting said reaction mixture with oxygen or oxygen-containing gases to form said bis-benzthiazolyl alkyl sulfenimides.

12. A process as claimed in claim 11, wherein at least one of said at least one of benzthiazolyl disulfides, 2-benzthiazolyl alkyl sulfenamides and 2-mercaptobenzthiazoles is substituted at the benzene ring by an alkyl radical, a halogen atom, a nitro group or an alkoxy group.

13. A process as claimed in claim 1, wherein the reaction is carried out in the presence of from about 0.01 to 1% by weight of the copper compound, based on the quantity of mercaptobenzthiazole used.

14. A process as claimed in claim 1, wherein the quantity of said at least one inert organic solvent used is from about 40 to 90% by weight, based on the total weight of the reaction mixture.

15. A process as claimed in claim 1, wherein the at least one organic solvent consists of at least one substance selected from the group consisting of hexane, cyclohexane, benzene, toluene, ethyl, methyl tert. butyl ether, acetonitrile, dimethyl formamide, tert. butyl amine and derivatives of tert. butyl amine.

* * * * *